United States Patent

Barton et al.

[11] 4,181,655
[45] Jan. 1, 1980

[54] 5(3-SUBSTITUTED AMINOPROPYL)-10-TRIFLUOROMETHOXY-5H-DIBENZ[b,f]AZEPINES

[75] Inventors: Derek H. R. Barton, London, England; Robert H. Hesse, Cambridge, Mass.

[73] Assignee: Research Institute for Medicine and Chemistry Inc., Cambridge, Mass.

[21] Appl. No.: 793,772

[22] Filed: May 4, 1977

Related U.S. Application Data

[63] Continuation of Ser. No. 500,189, Aug. 23, 1974, abandoned.

[30] Foreign Application Priority Data

Aug. 24, 1973 [GB] United Kingdom ............ 40242/73

[51] Int. Cl.² .............. C07D 223/26; C07D 401/06; C07D 403/06; C07D 413/06
[52] U.S. Cl. .......................... 260/239 D; 424/244; 260/326.5 CA; 544/111; 544/359; 544/200
[58] Field of Search ..................................... 260/239 D

[56] References Cited

FOREIGN PATENT DOCUMENTS 943276 12/1963 United Kingdom .
1024021 3/1966 United Kingdom .
1244642 9/1971 United Kingdom .

Primary Examiner—Donald G. Daus
Assistant Examiner—D. B. Springer
Attorney, Agent, or Firm—Bacon & Thomas

[57] ABSTRACT

Novel compounds of general formula

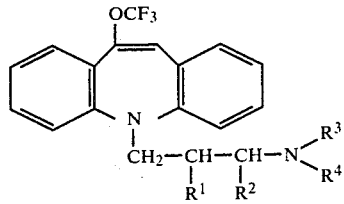

(where $R^1$ and $R^2$, which may be the same or different, are hydrogen atoms or alkyl groups; and $R^3$ and $R^4$, which may be the same or different, represent alkyl groups which may carry substituents, $R^4$ alternatively representing a hydrogen atom; or $R^3$ and $R^4$ together with the intervening N represent a heterocyclic group or an acid-addition salt thereof) are provided, together with a process for their preparation. The new compounds are useful as antidepressants.

7 Claims, No Drawings

5(3-SUBSTITUTED AMINOPROPYL)-10-TRIFLUOROMETHOXY-5H-DIBENZ[b,f]AZEPINES

This is a continuation, of application Ser. No. 500,189, filed Aug. 23, 1974, now abandoned.

This invention relates to novel dibenzazepines related to imipramine which have notable anti-depressant activity.

The new compounds are characterised in having a 10-Trifluoromethoxy substituent and a 10,11-double bond together with the 5-side chain and other nuclear substituents of imipramine and its analogues, and are thus 5-(3'-aminoprop-1'-yl)-10-trifluoromethoxy-5H-dibenz[b,f]azepines.

The compounds according to the present invention may, in general, be represented by the formula

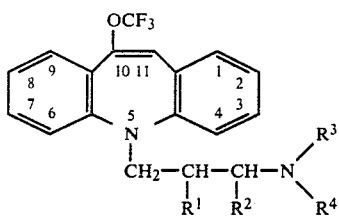   I where
$R^1$ and $R^2$ which may be the same or different are hydrogen atoms or alkyl groups; and
$R^3$ and $R^4$ which may be the same or different represent alkyl groups which may carry substitutents such as aryl groups, e.g. phenyl groups, or alkylamino groups, e.g. diethylamino or dimethylamino groups, $R^4$ alternatively representing a hydrogen atom; or $R^3$ and $R^4$ together with the intervening N represent a heterocyclic group. The nucleus may also optionally carry further substituents such as alkyl, alkoxy, or alkylthic groups or halogen atoms; and acid addition salts thereof.

$R^3$ and $R^4$ are preferably lower alkyl groups, e.g. with 1–6 carbon atoms such as methyl, ethyl, propyl, butyl, isopropyl, or hexyl groups, optionally carrying an aryl substituent, as in the benzyl or phenethyl groups, or a dialkylamino group such as a 2-diethylamino-ethyl or 2-dimethylaminoethyl group.

$R^3$ and $R^4$ together with the intervening N may represent a heterocyclic group such as a cyclic amine with 5 to 8 ring members, optionally containing further heteratoms. $R^3$ and $R^4$ may thus, for example, comprise a cyclic monoamine group such as a piperidine, pyrrolidine, hexamethylenimine or morpholine group or a cyclic diamine group such as a piperazine, N-alkylpiperazine or N-hydroxyalkylpiperazine, e.g. N-hydroxyethyl piperazine group.

$R^1$ and $R^2$ preferably represent hydrogen atoms or lower alkyl groups, e.g. with 1–6 carbon atoms, such as methyl groups.

The acid addition salts may be salts with mineral acids, e.g. hydrochloric, hydrobromic or sulphuric acid, or organic acids, e.g. maleic or tartaric acid.

Nuclear substituents which may be present include halogen atoms, especially chlorine atoms; alkyl groups such as methyl groups, alkoxy groups such as methoxy or ethoxy groups or alkylthio groups such as methylthio, ethylthio or isopropylthio groups. Such substituents are preferably in one or more of the 2-, 3-, 7- and 8-postions, for example, 2-chloro, 3-chloro, 7-chloro, 8-chloro, 3,7-dichloro, 2-methoxy or 3-methylthio substituents. The alkyl, alkoxy and alkyl groups preferably contain 1–6 carbon atoms.

The compounds according to the present invention preferably carry a 5-(3-dimethylaminopropyl)-side chain as in the preferred compound 5-(3-dimethylaminopropyl)-10-trifluoromethoxy-5H-dibenz[b,f]azepine.

The compounds exhibit notable anti-depressant activity and particularly low CNS side-effects, which renders them of particular interest in the treatment of depression states, in particular endogenous depression. Thus, the new compounds are tolerated at substantially higher doses than the related compound iminpramine, and being approximately equally active, so have an improved therapeutic ratio.

According to the further feature of the present invention we provide pharmaceutical compositions comprising a compound of the general formula I as defined above together with a pharmaceutical carrier or excipient. Suitable forms include the usual types of antidepressant formulation using especially the oral route, for example, tablets, coated tablets, capsules, syrups and elixirs. Formulations for injection may also be used. The compositions are preferably dosage unit forms, in particular tablets and coated tablets. Each dosage unit preferably contains 2.5 to 300 mg, advantageously 10 to 50 mg, especially 15–20 mg of active ingredient.

The compounds of general formula I may, in general, be prepared by the addition of trifluoromethyl hypofluorite across the 10,11-double bond of a 5-acyl-5H-dibenz[b,f]azepine using the method of British Patent Specification No. 1,244,642 to give a $CF_3OF$ adduct which on treatment to eliminate HF and the 5-acyl group gives an intermediate 10-trifluoromethoxy-5H-dibenz[b,f]azepine which may be reacted to introduce the appropriate 5-substituent.

According to a further feature of the present invention we provide a process for the preparation of a compound of the general formula I as defined above in which 10-trifluoromethoxy-5H-dibenz[b,f]azepine, i.e. a compound of the general formula

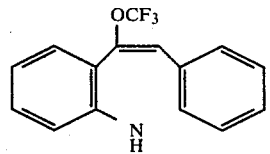   (II)

(where the nucleus may carry substitutents) or an N-alkali metal derivative thereof is reacted with an alkylating reagent serving to introduce a 3-substituted prop-1-yl e.g. a group of the formula

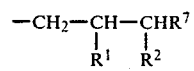

where $R^1$ and $R^2$ are as defined above and $R^7$ is a group $-NR^3R^4$ where $R^3$ and $R^4$ are as defined above, or a substitutent convertible into a group $-NR^3R^4$.

The alkylating reagent may conveniently be of the formula

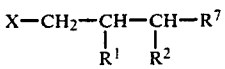

where X represents a reactive ester radical such as a halogen atom or an alkane sulphonyloxy or arylsulphonyloxy group, and $R^1$, $R^2$ and $R^7$ have the above meanings. The reaction is preferably effected in an aprotic solvent of high dielectric constant such as an ether, e.g. dimethyl ether, diethyl ether or tetrahydrofuran. A substituent convertible into a group —$NR^3R^4$ may, for example, be —$NH_2$ which may subsequently be alkylated, or a halogen atom (less reactive than X) which may subsequently be reacted with an amino $NR^3R^4$.

The reagent of formula II is preferably used in the form of an alkali metal derivative such as a sodium or potassium, derivative and such a metallated derivative may conveniently be obtained by reacting a compound of formula II in the NH form with a metallating agent such as an alkali metal hydride or alkyl.

An alternative process for the preparation of compounds of the general formula I as defined above comprises the reaction of a compound of the general formula

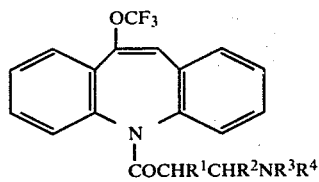

where $R^1$, $R^2$, $R^3$, $R^4$ and the optional nuclear substituents are as defined above, with a reagent serving to reduce an amide to an amine, e.g. a lithium aluminium hydride, diborane or the Bouveault-Blanc reagent.

The compounds of the general formula II may be obtained by reaction of a 5-acyl-5H-dibenz[b,f]azepine of the general formula

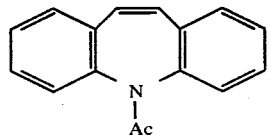

where Ac represents an acyl group, in particular a group —$COR^5$, where $R^5$ represents an alkyl, haloalkyl, aminoalkyl, alkoxy or aralkoxy group or a halogen atom and where the nucleus may carry substituents, with trifluoromethyl hypofluorite to form an intermediate of the general formula

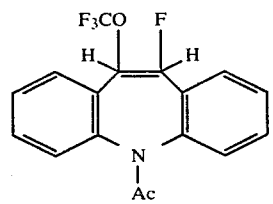

(where Ac is as defined above and the nucleus may carry substituents) which is subsequently reacted with a reagent serving to remove HF.

The reaction with the hypofluorite reagent initially yields a mixture of cis and trans isomers at the 9- and 10-positions but elimination of HF regenerates the 9,10-double bond in both isomers so that no separation is required, although the individual isomers can readily be isolated e.g. by chromatography or fractional crystallisation.

It will be seen that where Ac represents a group of the formula —$COCHR^1CHR^2NR^3R^4$, the product obtained is of the formula IV defined above. The acyl derivative of formula VI constitute important intermediates and are thus a further feature of the invention.

The acyl group may be removed, conveniently at the same time as the HF, by treatment under the appropriate conditions, although the HF may be eliminated while leaving the acyl group in position if a compound of formula IV is required. The halocarbonyl or alkoxycarbonyl group is particularly easy to remove by standard methods.

The reagent serving to remove HF may conveniently comprise an amine or a metal halide, hydroxide or alkoxide. For simultaneous removal of the acyl group stronger conditions should be chosen, for example, treatment with an alcoholic alkali metal hydroxide at elevated temperatures.

The following Examples illustrate the invention.

PREPARATION 1

N-Acetyl iminostilbene, (5-Acetal-5H-dibenz[b,f]azepine)

Iminostilbene(2 g) was added to a mixture of $Ac_2O$/pyridine 2:1(5 ml) and the solution was refluxed for 3 hours after which the solution was poured into water (100 ml) and the precipitate filtered off. This precipitate was purified by chromatography on silica gel eluted with chloroform to give the product as colourless needles, mp. 120°–121° C. (lit. 121°–122° C.); yield 2 g.

PMR: 7.4 (8Hm), 6.9(2Hs), 1.8(3Hs).

IR(KRr): $\nu_{max}$ 1680 cm$^{-1}$

UV(MeOH) $\lambda_{max}$=285 mµ ($\epsilon$=12,900).

PREPARATION 2

N-Ethoxycarbonyliminostilbene, (5-ethoxycarbonyl-5H-dibenz[b,f]azepine)

Iminostilbene (4 g) was added to sodium-dried toluene (300 ml) containing NaH(1 g.) The mixture was refluxed for 4 hours, after which the solution was a deep black colour. Ethyl chloroformate (3 ml) was slowly added until the black colour had disappeared. After the solution had cooled, the remaining NaH was destroyed by the slow addition of methanol. The solution was filtered and the residue washed with chloroform (50 ml). The toluene and chloroform solutions were combined and the solvent removed under vacuum. The resulting solid was dissolved in boiling hexane (200 ml) and the product (5 g) crystallised out on cooling: colourless needles; mp 130°–131° C. (lit, 126°–128° C.).

IR(KBr)$\nu_{max}$=1700 cm$^{-1}$.

PMR: 7.4 (8Hm) 6.90(2Hs) 4.10(2Hq.J=7 Hz) 1.12(3Htr.J=7 Hz)

UV(MeOH)$\lambda_{max}$=283 ($\epsilon$=10,000), 233 ($\epsilon$=15,800).

PREPARATION 3

Addition of trifluoromethyl hypofluorite to the products of Preparations 1 and 2

10 millimoles of the iminostilbene derivative were dissolved in 200 mls. of solvent containing CaO(0.5 g). The solution was cooled to −78° C. in a methylene chloride/dry ice bath with stirring. CF$_3$OF (300 ml ca. 70% pure) was bubbled into the solution via a water wash and a trap cooled to −78° C. The rate of addition was ca. 10 ml/min. The solution was then flushed with nitrogen for 20 min, brought to room temperature, washed with dilute aqueous sodium bicarbonate, dried over sodium sulphate and the solvent removed under vacuum. The resulting oil was then either chromatographed repeatedly on alumina or silica, or in the case of the N-ethoxycarbonyl adducts, crystallised from hexane. Yields ca.95%.

(a) N-acetyl-iminostilbene:

trans CF$_3$OF adduct: m.p. 100°–103° C. colourless crystals, mixed mp. with cis adduct less than 90° C.

IR $\nu_{max}$=1670, 1160–1270 cm$^{-1}$
M$^+$:339.03 C$_{17}$H$_{13}$F$_4$NO$_2$ requires 330.0
PMR: δ7.5(8Hm), δ5.0–6.8)2Hm), δ2.2(3Hm).

cis CF$_3$OF adduct: mp. 114–116C, colourless crystals.

IR: $\nu_{max}$=1670, 1160–1270 cm$^{-1}$
M$^+$=339.03
PMR. δ7.5(8HM), δ6.2–5.0(2Hm).δ2.0(3Hs)
Microanalysis:
C$_{17}$H$_{13}$F$_4$NO$_2$ requires: C 60.2%; H 3.84%; F 22.4%.
found for trans: C 60.21%; H 3.92%; F 22.22%; cis: C 60.17%; H 3.94%.

(b) N-Ethoxycarbonyl-iminostilbene trans CF$_3$OF adduct: colourless needles, mp. 107°–107.5° C.

IR (KBr): $\nu_{max}$=1710 cm$^{-1}$(s), 1100–1300 cm$^{-1}$(s)
UV(MeOH) $\nu_{max}$=268 (ε=1100), 235sh (ε=6960)
PMR: δ7.3(8Hm), δ6.3–δ4.8(2Hm), δ4.2(2Hq,J=7 Hz), δ1.2(3Htr.J=7 Hz)
FMR: φ*+67.2 and +68.8 ppm (two br.s.1:2, 3F) +180 (br.q.J=50,13 Hz) +206 (br.s.) (1F)

cis CF$_3$OF adduct; colourless rosettes of needles, mp. 133°–34° C. mmp with trans 90°–94° C.

UV(MeOH) 263(1000) 229sh(7830)
IR(KBr) 1705 cm$^{-1}$(s) 1150–1300 cm$^{-1}$(s)
PMR. δ7.4(8HM)δ6.5–5.3(2H, four br.s.)δ4.2(2Hq.,J=7 Hz)δ1.2 (3Htr. J=7 Hz.)
Fmr φ*+68.8,70.8(3F, two br.s.) +201–202.6(1F, four br.s)
Microanalysis. C$_{18}$H$_{15}$F$_4$NO$_3$ requires, C 58.54%, H4.09%, F 20.58% N 3.79%.
Found for trans, C58.59%, H4.25%, F20.26%, N3.78%.
cis, C58.09%, H4.08%, F20.90%, N3.65%.

cis fluoromethoxy adduct, isolated in up to 50% yield on fluorination in methanol, colourless rosettes of needles, m.p. 101°–102° C. corr.

IR(KBr) $\nu_{C=O}$1705 cm$^{-1}$
UV(MeOH) 267(890) 230sh(7840)
PMR. δ7.7–δ7.2(8Hm), [δ6.3 brs., δ5.5 brs., δ5.2 brs.) δ4.7d](OH)
δ4.2(2HqJ=7 Hz), δ3.6(3H Br.s.), δ1.2(3H br., J=7 Hz).
FMR. φ*202 ppm (br., J=25 Hz).

Microanalysis C$_{18}$H$_{18}$FNO$_3$ requires, C68.56%, H5.75%, F6.02%, N4.44%.
Found: C68.55%, H5.70%, F6.23%, N4.40%.

PREPARATION 4

Elimination of HF with base

N-ethoxycarbonyl iminostilbene (2.92 g) was allowed to react with CF$_3$OF (400 ml) in methylene chloride. The solvent was removed under vacuum and the remaining gum was dissolved in EtOH (150 ml) to which KOH (20 g) was added with stirring. The solution was refluxed overnight and the solvent was then removed under vacuum. The product was extracted from the residue with benzene (100 ml) and the benzene extract was washed with water (2×25 ml) and dried over magnesium sulphate. The solution was concentrated to 10 ml and chromatographed on silica (100 g) eluting with benzene/hexane (2:3). The fractions were examined by glc. (1.5%NGS; 200° C.) and it was found that 10-trifluoromethoxy iminostilbene (10-trifluoromethoxy-5H-dibenz[b,f]azepine was eluted first, yield 1.94 g (73%), as a yellow crystalline solid mp. 61°–62° C.

IR (KBr & CHCl$_3$ solution): $\nu_{max}$=3400 cm$^{-1}$w. 1220,1250 cm$^{-1}$s.
PMR: 7.4−6.3(9Hm) 4.97(1H br.s.)
UV(MeOH): $\nu_{max}$=255 (ε=39,600), 292sh (ε=3,680)
microanalysis:
C$_{15}$H$_{10}$F$_3$NO requires, C, 64.98%, H3.61%, F,20.58%, N,5.05%.
Found C, 64.97%, H3.44%, F,20.31%, N,4.98%.

The remaining fractions contained both 10-fluoro-iminostilbene and 10-trifluoromethoxy-iminostilbene. The 10-fluoro product was isolated tolerably pure (100 mg) as a yellow crystalline solid mp. 74°–76° C.

IR(KBr) $\nu_{max}$=3450 cm$^{-1}$w., 1060 cm$^{-1}$s.
PMR: 7.4−6.4 (8Hm) 6.22(1Hd,J=20 Hz) 5.1(1H br.s)
no satisfactory analysis was obtained.

EXAMPLE 1

5-(3-Dimethylaminopropyl)-10-trifluoromethoxy-5H-dibenz[b,f]azepine

10-Trifluoromethoxy-5H-dibenz[b,f]azepine (650 mg) was refluxed with NaH (600 mg, 57% suspension) in a solution of 3-dimethylaminopropyl chloride (ca. 2.0 g) in dimethyl ether (70 ml) overnight. The excess of NaH was destroyed with MeOH (10 ml) and the solvent removed under vacuum. The remaining gum was dissolved in ether (50 ml), washed with water (2×20 ml) and extracted into 2 N H$_2$SO$_4$ (2×20 ml). The extracts were combined, neutralized with NaHCO$_3$ and extracted with ether (3×20 mls). The ether extracts were washed with water (2×20 mls), dried (Na$_2$SO$_4$) and the ether removed under vacuum.

Yield 775 mg (95%) of a yellow oil. b.p. 90° at 80 torr.; n$_D$$^{26}$ =1.5525
UV(MeOH): λ$_{max}$254 (ε=26820), 281 (ε=3800), 347 (ε=480).
PMR: δ7.6−δ7.0(8Hm), δ6.9 (1H br.tr.½ to =4 Hz), δ3.8 (2H br.tr., J=7 Hz), δ2.4(2H br.tr., J=7 Hz) δ8.20 (6Hs), δ1.7 (2Hm).
IR (CCl$_4$): λ$_{max}$=1170, 1230 cm$^{-1}$(s) (OCF$_3$).

| microanalysis: | C | H | F | N |
| --- | --- | --- | --- | --- |
| C$_{20}$H$_{21}$F$_3$N$_2$O requires: | 66.28 | 5.84 | 15.73 | 7.73% |

| -continued | | | | |
|---|---|---|---|---|
| microanalysis: | C | H | F | N |
| Found: | 66.10 | 5.78 | 15.92 | 7.49% |

The free base was dissolved in ethanol and the solution treated with an ethanol solution of hydrogen chloride, followed by addition of ether to induce crystallisation of the hydrochloride salt so formed.

The corresponding maleate and tartrate salts were prepared similarly, using ethanol solutions of maleic and tartaric acid respectively.

EXAMPLE 2 Tablets

Composition:
1 tablets contains

| | |
|---|---|
| 5-(3-dimethylaminopropyl)10-trifluoromethoxy-5H-dibenz[b,f]azepine hydrochloride | 10.00 mg |
| lactose | 35.0 mg |
| potato starch | 49.0 mg |
| polyvinyl pyrrolidone | 5.0 mg |
| magnesium stearate | 1.0 mg |
| | 100.0 mg |

EXAMPLE 3 Coated Tablets

Composition:
1 tablet core contains

| | |
|---|---|
| 5-(3-dimethylaminopropyl)-10-trifluoromethoxy-5H-dibenz[b,f]azepine hydrochloride | 25.0 mg |
| lactose | 35.0 mg |
| polyvinyl pyrrolidone | 6.0 mg |
| corn starch | 13.0 mg |
| magnesium stearate | 1.0 mg |
| | 80.0 mg |

Tablets cores of this composition are coated with sugar and talcum and wax polished to give finished tablets of 120.0 mg.

EXAMPLE 4 Capsules

Capsules containing the same active ingredient as Examples 2 and 3 are prepared by mixing the active ingredient (20.0 mg per capsule) and lactose (80.0 mg per capsule) and filling standard gelatin 100 mg size capsules.

EXAMPLE 5 Ampoules for Intramuscular Injection

Each ampoule contains:

| | | |
|---|---|---|
| 5-(3-dimethylaminopropyl)-10-trifluoromethoxy-5H-dibenz[b,f]-azepine hydrochloride | | 10.0 mg |
| Ascorbic acid | | 0.5 mg |
| Sodium bisulphite | | 0.5 mg |
| Sodium sulphite | | 1.0 mg |
| Water for injection | ad | 2.0 ml |

We claim:

1. A compound of the formula:

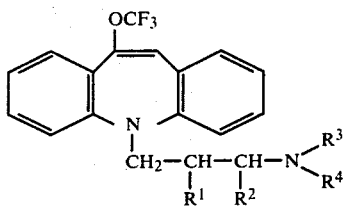

wherein $R^1$ and $R^2$ which may be the same or different are hydrogen atom or $C_{1-6}$ alkyl groups; and $R^3$ and $R^4$ which may be the same or different represent $C_{1-6}$ alkyl groups which may carry as substituents phenyl or di-$C_{1-6}$ alkylamino groups, $R^4$ alternatively representing a hydrogen atom; the nucleus of said compound may be unsubstituted or carry at least one substituent selected from the group consisting of $C_{1-6}$ alkyl, $C_{1-6}$ alkoxy, $C_{1-6}$ alkylthio and halogen atoms; or a physiologically acceptable acid addition salt thereof.

2. A compound as claimed in claim 1, in which $R^1$ and $R^2$ represent hydrogen atoms $R^3$ represents a methyl group and $R^4$ represents a methyl group or a hydrogen atom.

3. A compound as claimed in claim 2 namely 5-(3-dimethylaminopropyl)-10-trifluoromethoxy-5H-dibenz[b,f] azepine or a physiologically acceptable acid addition salt thereof.

4. The compound of claim 1, wherein the nucleus carries a further substituent selected from the group consisting of $C_{1-6}$ alkyl, $C_{1-6}$ alkoxy, $C_{1-6}$ alkylthio and halogen atoms.

5. A compound as claimed in claim 1, wherein the acid addition salt is formed from hydrochloric, hydrobromic, sulphuric, maleic or tartaric acid.

6. A compound as claimed in claim 4, wherein the substituents on the nucleus are substituted in one or more of the 2-, 3-, 7- and 8-positions.

7. A compound as claimed in claim 6, wherein the substituents are 2-chloro, 3-chloro, 7-chloro, 8-chloro, 3,7-dichloro, 2-methoxy or 3-methylthio substituents.

* * * * *